US00PP30004P2

(12) United States Plant Patent
Coniff

(10) Patent No.: US PP30,004 P2
(45) Date of Patent: Dec. 18, 2018

(54) ***ALOE* PLANT NAMED 'OVROCKS04'**

(50) Latin Name: ***Aloe* hybrid**
Varietal Denomination: OVROCKS04

(71) Applicant: Ovata B.V., Bleiswijk (NL)

(72) Inventor: Kevin Coniff, Jamul, CA (US)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/932,018

(22) Filed: Jan. 25, 2018

(51) Int. Cl.
*A01H 5/00* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct variety of *Aloe* plant named 'OVROCKS04' which is characterized by a broad obovate plant form with foliage arranged in an upright basal rosette, dark green succulent foliage bearing small light green protuberances and large white spine-like teeth along the leaf margins, and the stability of these characteristics from generation to generation.

2 Drawing Sheets

Latin name of the genus and species: The Latin name of the genus and species of the novel variety disclosed herein is *Aloe* hybrid.

Variety denomination: The inventive variety of *Aloe* disclosed herein has been given the variety denomination 'OVROCKS04'.

BACKGROUND OF THE INVENTION

Parentage: 'OVROCKS04' is a seedling selection resulting from the controlled pollination of an unnamed *Aloe striata* plant (unpatented), the seed parent, with *Aloe* hybrid Hercules (unpatented), the pollen parent. The crossing was made by the inventor in January of 2010 at a greenhouse in Fallbrook, Calif. In March of 2011, one seedling was observed which exhibited a unique growth habit and substantially different foliage characteristics when compared to the parent plants and all other progeny. After confirming the stability of the unique characteristics first observed, the new plant was selected for commercialization and given the name, 'OVROCKS04'.

Asexual Reproduction: Asexual reproduction of the new cultivar 'OVROCKS04', by way of rooting leaf cuttings, was first initiated in March of 2010 at a commercial greenhouse in Bleiswijk, the Netherlands. The claimed plant has since been asexually propagated by way of meristematic tissue culture propagation. Through five subsequent generations, the unique features of this cultivar have proven to be stable and true to type.

SUMMARY OF THE INVENTION

The cultivar 'OVROCKS04' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS04'. These characteristics in combination distinguish 'OVROCKS04' as a new and distinct *Aloe* cultivar:

1. 'OVROCKS04' exhibits a broad obovate plant form with foliage arranged in a basal rosette; and
2. 'OVROCKS04' exhibits dark green succulent foliage which is held upright; and
3. 'OVROCKS04' exhibits coarsely dentate leaf margins with an abundance of white spine-like teeth; and
4. 'OVROCKS04' exhibits small light green protuberances along the midrib of the upper leaf surface; and
5. 'OVROCKS04' exhibits a moderate abundance of small yellow-green protuberances on the lower leaf surface.

BOTANICAL DESCRIPTION OF THE PLANT

Figure 1:
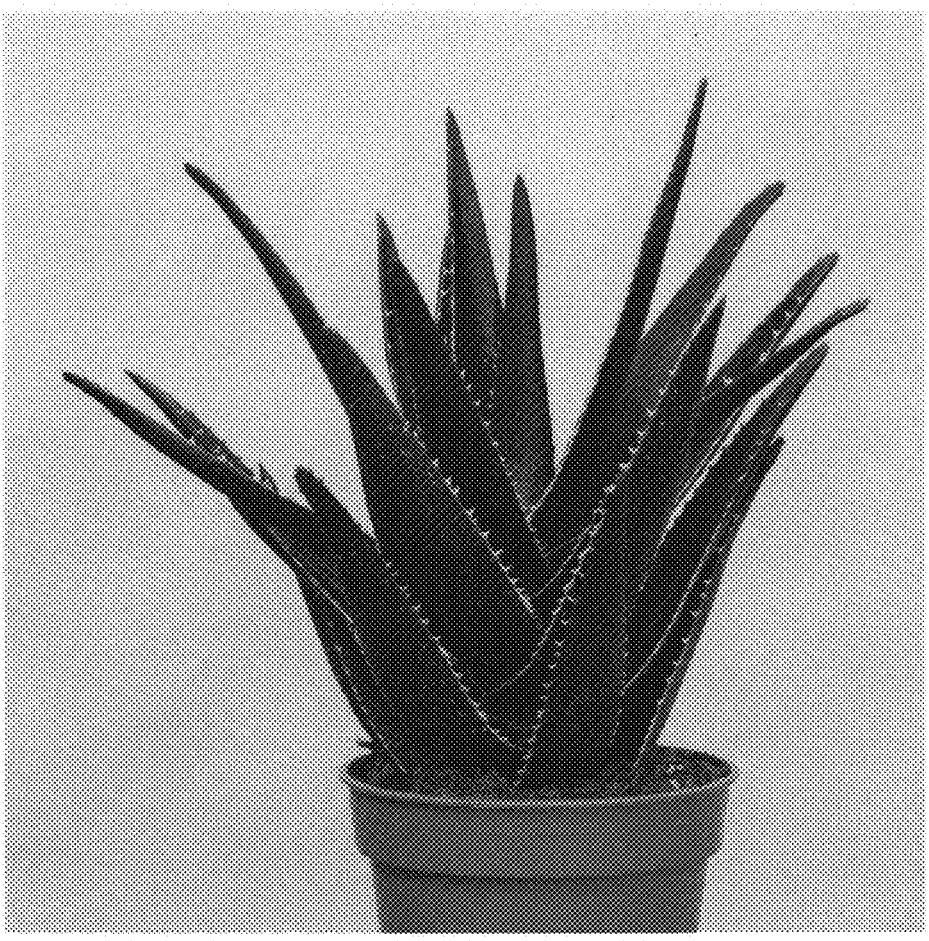
FIG. 1 illustrates, as nearly true as it is reasonably possible to make the same in color photographs of this type, an exemplary plant of 'OVROCKS04' grown in a commercial greenhouse in Bleiswijk, the Netherlands. This plant is approximately 18 months old, shown planted in a 17 cm container.
Figure 2:
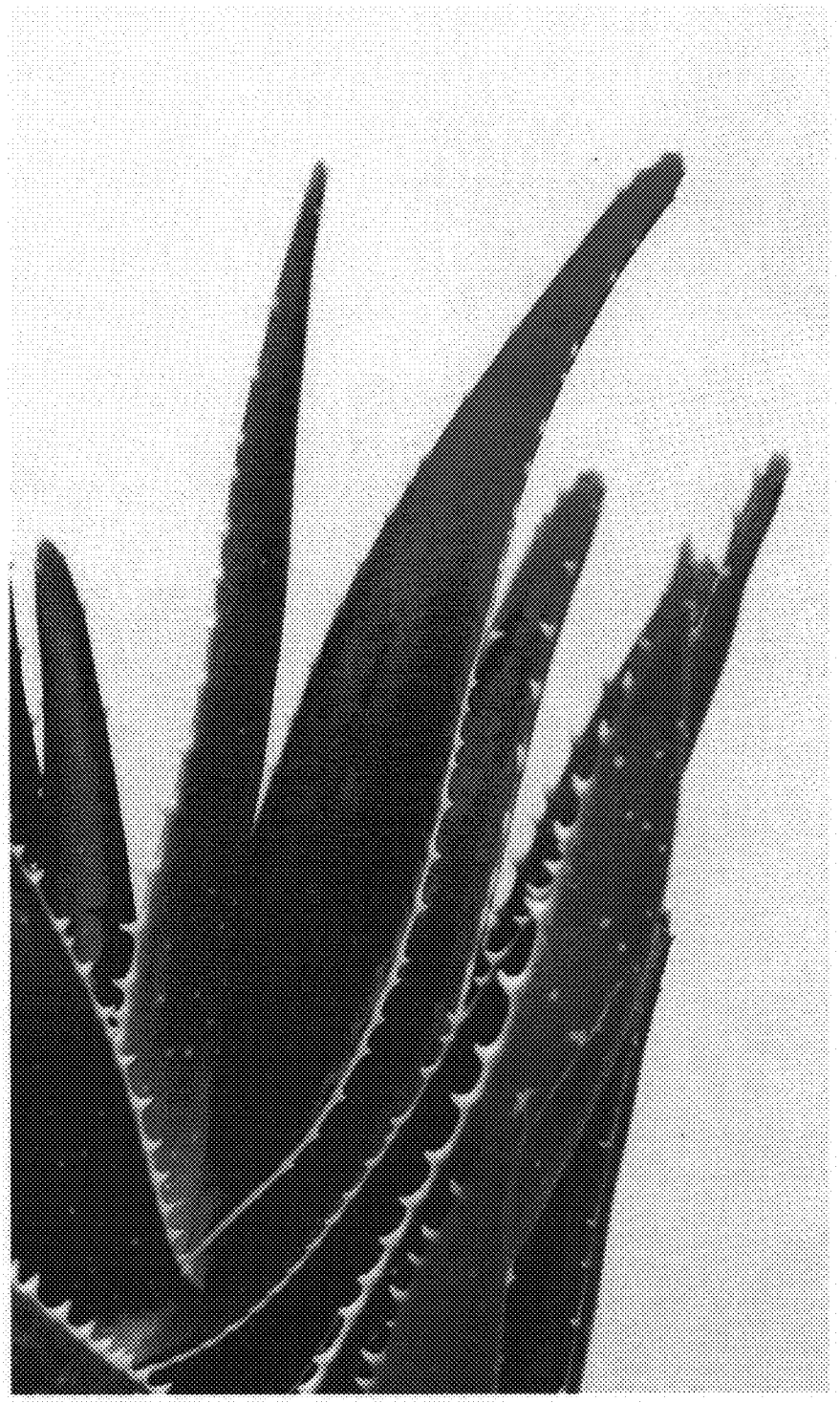
FIG. 2 illustrates, as nearly true as it is reasonably possible to make the same in color photographs of this type, the typical foliage of 'OVROCKS04'.

The following observations and measurements made in June of 2017 describe averages from a sample set of six specimens of 18 months old 'OVROCKS04' plants grown in 17 cm nursery containers at a commercial greenhouse in Bleiswijk, the Netherlands. Plants were produced using conventional greenhouse production protocols for *Aloe* which consisted of minimal overhead irrigation and fertilizer applications. No pest or disease control measures were utilized in production. Plants were grown under partial shade (approximately 20,000 lux) and no photoperiodic treatments or artificial light was given to the plants.

Those skilled in the art will appreciate that certain characteristics will vary with older or, conversely, with younger plants. 'OVROCKS04' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS04' and comparisons with the parents and closest known comparator are provided below.

Plant description:

*Growth habit*.—Succulent perennial with foliage growing in an upright, non-branched basal rosette, eventually forming a stem-like structure.

*Plant form*.—Broad obovate.

*Height from soil level to top of foliar plane*.—29.6 cm.

*Plant spread*.—Average of 30.9 cm.

*Growth rate*.—Moderate.

*Plant vigor*.—Moderate.

*Propagation*.—Type — Leaf cuttings. Time to initiate rooting — Approximately 2 months at 21 degrees Celsius. Crop time — Approximately 18 months to produce a marketable plant in a 9 cm container.

*Disease and pest resistance or susceptibility*.—Neither resistance nor susceptibility to typical *Aloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a basal rosettes, eventually forming a short, unbranched stem with age; no lateral branching.

*Quantity of main stems*.—1.

*Quantity of lateral branches*.—None.

*Main stem dimensions*.—10.0 cm long and 2.3 cm in diameter.

*Internode length*.—0.6 cm.

*Cross section*.—Rounded, formed by leaf sheaths.

*Attitude*.—Nearly vertical.

*Strength*.—Very strong.

*Texture and luster*.—Glabrous and matte.

*Color, when developing*.—Yellow-green, nearest to RHS 150D.

*Color of mature stem*.—Nearest to in between yellow-green, RHS 150D, and green-white, RHS 157D.

*Color at internodes*.—Nearest to in between yellow-green, RHS 150D, and green-white, RHS 157D.

Foliage:

*Arrangement*.—Spirally placed in a rosette.

*Division*.—Simple.

*Attachment*.—Sessile.

*Quantity*.—Approximately 22 leaves per rosette.

*Shape*.—Lanceolate succulent leaves.

*Dimensions*.—22.4 cm long, 4.9 cm wide, and 1.0 cm thick, on average.

*Aspect*.—Flat to slightly concave.

*Attitude*.—At an average angle of 50 degrees to the soil level.

*Apex*.—Narrow bluntly acute, with an average of 4 soft mucronate tips.

*Base*.—Sheathing.

*Sheath*.—Sheath dimensions — 2.5 cm long and 1.4 cm wide, on average. Sheath color — Yellow-green, nearest to RHS 150D.

*Margin*.—Coarsely dentate; prominent teeth have an average length of 0.3 cm and are colored white, nearest to RHS 155C. Margins are not undulated or lobed.

*Texture, adaxial surface*.—Glabrous; midrib is occasionally very sparsely to sparsely covered with protuberances, presenting as small soft spines; on average, spines are 0.1 cm in diameter and 0.1 cm high.

*Texture, abaxial surface*.—Glabrous; veins are moderately covered with protuberances, presenting as small soft spines; on average, spines are 0.1 cm in diameter and 0.1 cm high.

*Luster, adaxial surface*.—Slightly glossy.

*Luster, abaxial surface*.—Slightly glossy.

*Color*.—Juvenile foliage, adaxial surface — Green, nearest to RHS NN137A, and fading to yellow-green towards the base, nearest to RHS 144B. Juvenile foliage, abaxial surface — Green, nearest to a combination of RHS NN137A and NN137B, and fading to yellow-green towards the base, nearest to a combination of RHS 144B and 144C; protuberances are colored yellow-green, nearest to RHS 145C. Mature foliage, adaxial surface — Nearest to in between green, RHS NN137A, and yellow-green, RHS 147A; spines are yellow-green, nearest to a mixture of RHS 144A and 144B. Mature foliage, abaxial surface — Nearest to in between green, RHS NN137A, and yellow-green, RHS 147A; spines are yellow-green, nearest to a mixture of RHS 144A and 144B. Venation — No venation is visible. Pattern — Parallel; only the midrib is visible on the adaxial surface. Color, adaxial surface — Nearest to in between green, RHS NN137A, and yellow-green, RHS 147A, but considerably darker. Color, abaxial surface — Nearest to in between green, RHS NN137A, and yellow-green, RHS 147A, but slightly darker.

*Petiole*.—No petiole; leaves are sessile.

Inflorescence: No flowering has been observed to date.

COMPARISONS WITH THE PARENT PLANT

Plants of the new cultivar 'OVROCKS04' differ from the seed parent, an unnamed *Aloe striata* plant (not patented), in the following characteristics described in Table 1 below.

COMPARISON WITH SEED PARENT

TABLE 1

| Characteristic | 'OVROCKS04' | The seed parent. |
|---|---|---|
| General coloration of entire rosette. | Darker green. | Lighter green. |
| Foliage size. | Smaller than the seed parent. | Larger than 'OVROCKS04'. |

TABLE 1-continued

| Characteristic | 'OVROCKS04' | The seed parent. |
|---|---|---|
| Foliage margins. | Coarsely dentate with larger, more prominent teeth. | Dentate with smaller, less prominent teeth. |

Plants of the new cultivar 'OVROCKS04' differ from the pollen parent, *Aloe* 'Hercules' (not patented), in the following characteristics described in Table 2 below.

COMPARISON WITH POLLEN PARENT

TABLE 2

| Characteristic | 'OVROCKS04' | 'Hercules' |
|---|---|---|
| Foliage attitude. | More upright than 'Hercules'. | Less upright than 'OVROCKS04'. |
| General coloration of entire rosette. | Darker green. | Lighter green. |
| Abundance of foliage. | More abundant. | Less abundant. |
| Foliage size. | More narrow than the pollen parent. | Wider than 'OVROCKS04'. |
| Presence of spine-like protuberances on the foliage. | Present. | None present. |
| Foliage margins. | Coarsely dentate, with prominent teeth. | Entire; not dentate. |

COMPARISONS WITH THE CLOSEST KNOWN COMPARATOR

Plants of the new cultivar 'OVROCKS04' differ from the commercial variety, *Aloe rauhii* 'OVALJAWS' (U.S. Plant Pat. No. 28,328) in the following characteristics described in Table 3 below.

COMPARISON WITH COMPARISON PLANT

TABLE 3

| Characteristic | 'OVROCKS04' | 'OVALJAWS' |
|---|---|---|
| Growth habit. | Less compact. | More compact. |
| Abundance of the spine-like protuberances on the foliage. | More abundant on the abaxial leaf surface. | Less abundant on the abaxial leaf surface. |
| Length of foliage. | Longer than 'OVALJAWS' | Shorter than 'OVROCKS04'. |
| Foliage margins. | Coarsely dentate with larger spine-like teeth. | Dentate with smaller spine-like teeth. |
| General coloration of teeth along the leaf margins. | White, nearest to RHS 155C. | White, nearest to RHS NN155D. |

That which is claimed is:

1. A new and distinct variety of *Aloe* plant named 'OVROCKS04', substantially as described and illustrated herein.

* * * * *